United States Patent [19]

Kuchino et al.

[11] Patent Number: 5,861,307
[45] Date of Patent: Jan. 19, 1999

[54] HUMAN S-MYC-LIKE POLYPEPTIDE AND A GENE CODING FOR SAID POLYPEPTIDE

[75] Inventors: Yoshiyuki Kuchino, Yokohama; Shigehide Kagaya, Yono, both of Japan

[73] Assignees: President of National Cancer Center; Nippon Kayaku Kabushiki Kaisha, both of Tokyo, Japan

[21] Appl. No.: 518,967

[22] Filed: Aug. 24, 1995

[30] Foreign Application Priority Data

Aug. 31, 1994 [JP] Japan .................................. 6-207236

[51] Int. Cl.$^6$ ..................................................... C12N 15/63
[52] U.S. Cl. ........................ 435/320.1; 435/325; 435/455; 435/69.1; 435/458; 536/23.1; 514/44
[58] Field of Search ........................... 514/44; 435/320.1, 435/172.3, 240.2, 62, 10, 32, 455, 69.1, 458

[56] References Cited

PUBLICATIONS

Proc. Natl. Acad. Sci. USA, 86, 9144–9148 (1989) Sugiyama, et al.
Proc. Natl. Acad. Sci. USA, 84, 7413–7417 (1987), Felgner, et al.
Baker et al. (The Study of Biology, fourth edition, Addison–Wesley Publishing Company, Inc., p. 9, 1982).
Watson et al., Recombinant DNA, second edition, Scientific American Books, p. 590, 1992
Ngo et al., in: *The Protein Folding Problem and Tertiary Structure Prediction,* 1994, Merz et al., (ed.), Birkhauser, Boston, MA, pp. 433 and 492–495).
Coghlan, New Scientist, Nov. 1995:13–14, vol. 148.
Marshall, Dec. 1995 Science: 1751, vol. 270.
Ledley, Hum. Gene. Ther. 1995, 6:1129–1144.
Mastrangel et al. Seminars in Oncology, vol. 23, 1:4–21, 1996.
Jain et al. Scientific America, 271(1):58–63, 1994.
Morton et al. Genomics 4, 1989:367–375, 1989.
Asai et al. Oncogene, Aug. 10, 1994, 9:2345–2352.

*Primary Examiner*—Christopher S. F. Low
*Assistant Examiner*—Dave Trong Nguyen
*Attorney, Agent, or Firm*—Nields, Lemack & Dingman

[57] ABSTRACT

Human s-myc-like gene, mycL2 (SEQ ID NO: 3) was isolated and identified from human placenta genomic DNA by PCR and human s-Myc-like polypeptide MycL2 (SEQ ID NO: 2) as the expression product of the gene was identified. The genetic DNA embedded in liposome can be targeted to glioma cells to prevent the growth of tumor cells or cause apotosis.

16 Claims, 6 Drawing Sheets

|   | Met | Asp | Arg | Asp | Ser | Tyr | His | His | Tyr | Phe | Tyr | Asp | Tyr | Asp | Gly | Gly |
|---|---|---|---|---|---|---|---|---|---|---|---|---|---|---|---|---|
| I |   |   |   |   | 5 |   |   |   |   | 10 |   |   |   |   | 15 |   |
|   | Glu | Asp | Phe | Tyr | Arg | Ser | Thr | Thr | Pro | Ser | Glu | Asp | Ile | Trp | Lys | Lys |
|   |   |   |   | 20 |   |   |   |   | 25 |   |   |   |   | 30 |   |   |
| II | Phe | Glu | Leu | Val | Pro | Pro | Trp | Asp | Leu | Gly | Pro | Ala | Ala | Gly | Asn |
|   |   |   | 35 |   |   |   |   | 40 |   |   |   |   | 45 |   |   |

Pro Ala Leu Ser Phe Gly Leu Leu Glu Pro Trp Pro Val Gly Cys Ala
     50              55              60

Gly Asp Glu Thr Glu Ser Gln Asp Tyr Trp Lys Ala Trp Asp Ala Asn
65              70 III       75              80

Tyr Ala Ser Leu Ile Arg Arg Asp Cys Met Trp Ser Gly Phe Ser Thr
            85          90            95

Gln Glu Pro Leu Glu Arg Ala Val Ser Asp Leu Leu Ala Val Gly Ala
          100         105         110

Pro Arg Gly Tyr Ser Pro Lys Glu Phe Ala Thr Pro Asp Tyr Thr Pro
       115         120         125

Glu Leu Glu Ala Gly Asn Leu Ala Pro Ile Phe Pro Cys Leu Leu Gly
   130            135         140 IV

Glu Pro Lys Ile Gln Ala Cys Ser Arg Ser Glu Ser Pro Ser Asp Ser
145          150         155         160

Glu Gly Glu Glu Ile Asp Val Thr Val Lys Lys Arg Gln Ser Leu Ser
            165        170         175

Thr Arg Lys Pro Val Ile Ile Ala Val Arg Ala Asp Leu Leu Asp Pro
       180       V 185         190

Arg Met Asn Leu Phe His Ile Ser Ile His Gln Gln His Asn Tyr
     195          200         205

Ala Ala Pro Phe Pro Pro Glu Ser Cys Phe Gln Glu Gly Ala Pro Lys
   210            215         220

FIG. IA

```
     Arg Ile Pro Pro Lys Glu Ala Leu Glu Arg Glu Ala Pro Gly Gly Lys
     225             230             235             240
     Asp Asp Lys Glu Asp Glu Glu Ile Val Ser Leu Pro Pro Val Glu Ser
                     245             250             255
     Glu Ala Ala Gln Ser Cys Gln Pro Lys Pro Ile His Tyr Asp Thr Glu
                 260             265             270
     Asn Trp Thr Lys Lys Lys Tyr His Ser Tyr Leu Glu Arg Lys Arg Arg
VI       275             280             285
     Asn Asp Gln Arg Ser Arg Phe Leu Ala Leu Arg Asp Glu Val Pro Ala
         290             295             300
     Leu Ala Ser Cys Ser Arg Val Ser Lys Val Met Ile Leu Val Lys Ala
     305             310             315             320
VII  Thr Glu Tyr Leu His Glu Leu Ala Glu Ala Glu Arg Met Ala Thr
                     325             330             335
     Glu Lys Arg Gln Leu Glu Cys Gln Arg Arg Gln Leu Gln Lys Arg Ile
VIII             340             345             350
     Glu Tyr Leu Ser Ser Tyr
             355
```

FIG. IB

HUMAN S-MYC-LIKE POLYPEPTIDE AND A GENE CODING FOR SAID POLYPEPTIDE

CROSS-REFERENCE

The present application relies for the priority upon the inventors' Japanese Patent Application No. 6-207236 filed Aug. 31, 1994, the content of which is herein incorporated by reference.

BACKGROUND OF THE INVENTION

1. Field of the Invention

The present invention relates to a human s-myc-like polypeptide (hereinafter often referred to as MycL2) which is effective for the treatment of tumors, especially glioma and lung cancer, and to a human s-myc-like polypeptide gene (hereinafter often referred to as mycL2) coding for the amino acid sequence of said polypeptide.

2. Description of the Related Art

From a standpoint that a cause of a cancer or a tumor already exists in genome DNA of normal cells, a gene that gives an instruction of oncogenesis of the cells to cause the development and growth of a cancer or a tumor is termed an oncogene. In the specification, a myc gene is treated as an oncogene.

As an oncogene that causes gene amplification in various tumors such as human leukemia, lung cancer, gastric cancer, etc., c-myc is known and this oncogene forms a series of oncogene family together with N-myc, L-myc, V-myc, etc.

Apart of these oncogenes which cause the development and growth of a cancer or a tumor, s-myc gene is known to be a carcinostatic gene having an activity of preventing the growth of a cancer or inducing apotosis (programmed death of cells) of tumor cells.

The s-myc gene is a myc-associated gene first isolated and identified from a rat gene library in 1989, which is an intron-free genetic DNA encoding the amino acid sequence of a nucleoprotein (s-Myc) consisting of 429 amino acids (Sugiyama et al., Proc. Natl. Acad. Sci. USA, 86, 9144–9148 (1989)).

On the other hand, studies have also been made on a new method for transfection which comprises inserting a specific DNA into an expression vector for animal cells, embedding this expression vector in the inside of liposome composed of a synthetic cationic lipid, and transfecting the expression vector into tumor cells or into a living body together with the tumor cells thereby to effect the insertion and expression of the DNA (hereinafter referred to as lipofection or liposome-mediated transfection, see Felgner et al., Proc. Natl. Acad. Sci. USA, 84, 7413–7417 (1987)).

In particular, it is reported that the liposome-mediated transfection exhibits, when applied to a rat s-myc gene, therapeutic effects specific to a glioma which is one of brain tumors. Recently, attention has thus been brought to the liposome-mediated transfection as a promising treatment for intractable tumor diseases coupled with a genetic treatment in vivo.

However, human s-Myc-like polypeptide showing a carcinostatic action or apotosis-inducing activity against tumor has not yet been found and its isolation and identification have been desired (hereinafter these activities possessed by this peptide are collectively referred to as a human s-Myc-like polypeptide activity and this polypeptide is referred to as MycL2). Furthermore, mycL2 gene coding for the amino acid sequence of the polypeptide is yet unknown. It has thus been strongly desired to isolate and identify the aforesaid gene and to develop a pharmaceutical composition and method for the treatment of a tumor having a high specificity.

SUMMARY OF THE INVENTION

An object of the present invention is to provide MycL2 (SEQ ID NO: 2) which is a human s-Myc-like polypeptide.

Another object of the present invention is to provide mycL2 gene (SEQ ID NO: 3) which codes for the amino acid sequence of MycL2.

A further object of the present invention is to provide a recombinant vector bearing DNA which has a nucleotide sequence encoding domain IV (SEQ ID NO: 7) of MycL2 and encoding the sequence of amino acids 119–191 (SEQ ID NO: 1).

A still further object of the present invention is to provide a highly specific pharmaceutical composition for the treatment of tumors, using mycL2 gene (SEQ ID NO: 3).

The present inventors have acquired cDNA of mycL2 (SEQ ID NO: 3) from human placenta-derived genomic DNA by PCR and succeeded in cloning mycL2 by genetic manipulation technology. It has been found that this mycL2 can be introduced into an expression vector of animal cells and tumor cells can be transfected by liposome-mediated transfection thereby to induce apotosis. The present invention has thus been accomplished.

BRIEF DESCRIPTION OF THE DRAWINGS

FIG. 1 shows a primary structure of MycL2 polypeptide (SEQ ID NO: 2) and domains I to VIII (SEQ ID NOS: 4–11).

DETAILED DESCRIPTION OF THE INVENTION

Figure 2:
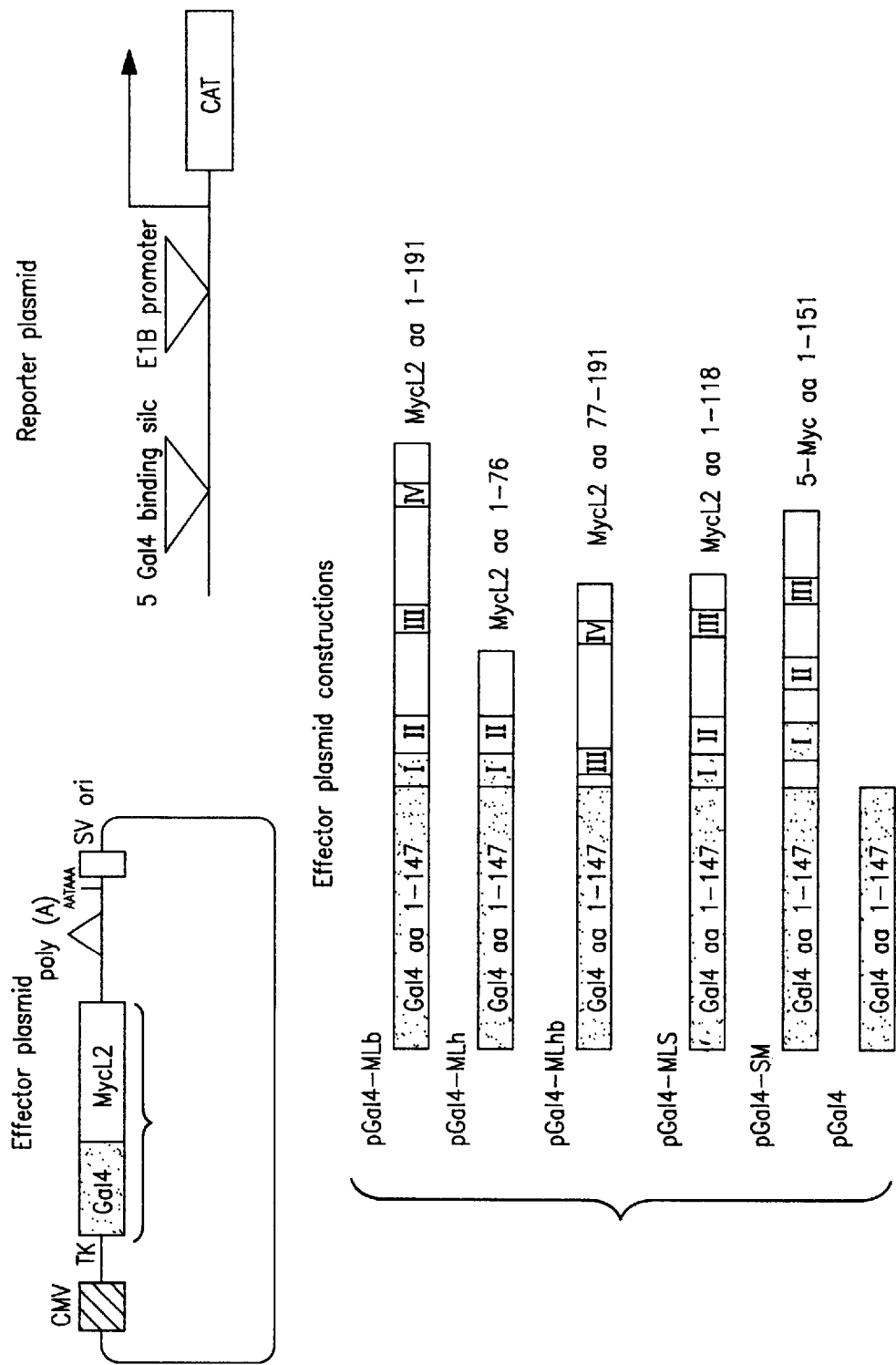
FIG. 2 shows the constructions of expression vectors pGal4-MLb, -MLh, -MLhb, -MLS and -SM as effector plasmids and Gal to be fused, and a partial construction of the regulator gene at the 5' end of CAT expression gene as a reporter plasmid.

As shown in FIG. 1, the amino acid sequence of the human s-Myc-like polypeptide (MycL2) according to the present invention comprises 358 amino acids (SEQ ID NO: 2) containing 8 domains (I through VIII) (SEQ ID NOS: 4–11).

Domains I to III (SEQ ID NOS: 4–6) designate domains for activation of transcription; Domain IV (SEQ ID NO: 7) is the one of acidic amino acids; Domain V (SEQ ID NO: 8) is a nuclear transfer signal; Domain VI (SEQ ID NO: 9) is a region of basic amino acids; Domain VII (SEQ ID NO: 10) has a helix-loop-helix structure; and Domain VIII (SEQ ID NO: 11) constructs a leucine zipper. Domains V (SEQ ID NO: 8), VI (SEQ ID NO: 9) and VII (SEQ ID NO: 10) are regions for DNA ligation and, Domains VII (SEQ ID NO: 10) and VIII (SEQ ID NO: 11) are protein-binding regions.

In Domain I (SEQ ID NO: 4), 20 Tyr corresponds to a site for phosphorylation (hereinafter referred to as phosphorylation site) with tyrosine kinase; in Domain IV (SEQ ID NO: 7) 158 Ser and 160 Ser with casein kinase; and in Domain VI (SEQ ID NO: 9), 271 Thr with casein kinase.

In the leucine zipper of Domain VIII (SEQ ID NO: 11), Met and three Leu groups surrounded by the solid line are important for constructing the zipper structure but the kind of amino acids outside the solid line and surrounded by the dashed line hardly affects the zipper structure.

In L-myc which is a myc-associated gene, two Ser groups located at both ends in the sequence of Ser-Pro-Pro-Thr-Ser (SEQ ID NO: 12) in Domain II are phosphorylation sites and in c-myc, Thr and Ser located at both ends in the sequence of Thr-Pro-Pro-Leu-Ser (SEQ ID NO: 13) in Domain II are phosphorylation sites; whereas in mycL2 (SEQ ID NO: 2) of the present invention, no such phosphorylation site associated with Domain II (SEQ ID NO: 5) is present.

In addition to MycL2 (SEQ ID NO: 2), the present invention also covers MycL2 derivatives containing the amino acid sequence shown in FIG. 1 as the major sequence and MycL2 derivatives having one or more amino acids replaced, deleted or inserted and having a human s-Myc-like polypeptide activity.

MycL2 (SEQ ID NO: 2) and its derivatives according to the present invention may vary in length of the polypeptide and amino acid composition unless the human s-Myc-like polypeptide activity of these derivatives are adversely affected. Such modified polypeptides are also included in the present invention.

These derivatives may be muteins of MycL2 (SEQ ID NO: 2) between the same species or between several species, or may be those obtained by replacing one or more starting amino acids in the amino acid sequence with other amino acids or deleting these starting amino acids, in a conventional manner in the polypeptide synthesis of MycL2, or those obtained by adding a new starting amino acid(s) to the amino acid sequence.

The present invention also relates to a human s-myc-like gene (mycL2) coding for the amino acid sequence of MycL2 polypeptide. mycL2 is DNA having a nucleotide sequence represented by SEQ ID NO:3.

The present invention includes not only mycL2 which is the structural gene nucleic acid (DNA) (SEQ ID NO: 3) but also nucleic acid (RNA) in which T in the nucleic acid (SEQ ID NO: 3) is replaced with U, nucleic acids (cDNA and cRNA) having nucleotide sequences complementary to these nucleic acids (DNA and RNA), fragments of the aforesaid nucleic acids which are selectively hybridized to mycL2, and modified products thereof.

The DNA of the present invention may be any of single-stranded DNA, double-stranded DNA and a vector such as a plasmid, etc., so long as it contains the nucleic sequence described above.

The DNA of the present invention can be used to express MycL2 polypeptide in a host such as an animal cell.

The mycL2 DNA of the present invention can be prepared, for example, as follows.

(a) The desired DNA bearing mycL2 having the nucleotide sequence of SEQ ID NO: 3 is isolated from human placenta-genomic DNA and inserted into an appropriate vector.

(b) Competent cells are transformed with the resulting vector to obtain mycL2-bearing vector. The DNA of mycL2 gene is excised using a restriction enzyme.

The thus excised DNA is ligated downstream the promoter or enhancer of the vector, whereby a mycL2 gene-bearing vector for transfection can be prepared.

The vector is transfected to, e.g., an animal cell. By culturing the resulting transfectant, MycL2 polypeptide can be produced. As a promoter upon producing MycL2 polypeptide in an animal cell, any promoter may be used basically as long as it functions in the animal cell but preferred are metallothionein (MT) and cytomegalovirus (CMV) promoters.

Where the mycL2 gene (SEQ ID NO: 3) of the present invention is applied to warm-blooded animal, especially human, as a pharmaceutical composition for the treatment of tumor, the mycL2 gene or the domain responsible for transcription inhibition is inserted into an animal cell expression vector and the vector is treated with liposome to either embed the vector within the liposome or bind the vector to the liposome through ionic bond, thereby to form the liposome-DNA complex containing the aforementioned vector together with the liposome, and the complex is transfected to cells same as or analogous to a target tumor. The thus transfected cells can be administered to reach the tumor.

Administration is effective by means of topical injection within a tumor, intramuscular injection into arms, legs, etc., pellets or intracutaneous injection. In the present invention, topical injection into a tumor and intramuscular injection are preferred.

A dose may vary depending upon size of cancer or tumor but the therapeutic effect can be expected in a smaller dose than that required from the size of tumor, since the pharmacological action of the composition is exhibited mainly based on apotosis which enhances immune response. In general, a dose for single topical injection or single intramuscular injection is in a range of approximately 0.1 μg to 2 mg, when calculated as the liposome containing the gene. Administration is effected by about once a week to once for 3 weeks. The dose and administration interval may be appropriately varied.

The gene-containing liposome used for the treatment may be stored at 4° C. to −80° C. until it is used. Alternatively, it may be stored in the form where a tumor cell is transfected; in this case, it may be stored in a frozen state at −80° C. to liquid nitrogen temperature. For the purpose of improving stability, various additives, e.g., an excipient for pharmaceutical use, a buffer or the like may also be added to the composition.

Where the liposome-DNA complex containing the mycL2 gene (SEQ ID NO: 3) of the present invention together with liposome is administered to the affiliated region, MycL2 polypeptide (SEQ ID NO: 2) produced by expression of mycL2 can induce a humoral factor of the immune system to specifically cause death of not only glioma cells at the site administered but also other glioma cells.

For example, where human-derived glioma cells U251 is transfected with the liposome-DNA complex in which a plasmid bearing mycL2 gene is embedded, it is confirmed that MycL2 polypeptide is expressed and the cells cause apotosis, not necrosis due to a cancer.

Furthermore, disappearance of the transcription activity results pharmacologically in, e.g., inhibition of the growth of a tumor. A recombinant vector bearing DNA containing a nucleotide sequence encoding Domain IV (SEQ ID NO: 7) or a sequence of amino acids 119–191 (SEQ ID NO: 1) containing Domain IV (SEQ ID NO: 7) is also useful as an active component of a composition for preventing the growth of a tumor.

Hereinafter the process for producing the DNA of the present invention and its expression will be described by referring to the following examples, wherein restriction enzymes made by Takara Shuzo Co., Ltd. were employed unless otherwise indicated.

(1) Isolation of DNA Bearing MycL2

DNA bearing mycL2 was isolated from human placenta genomic DNA (CL6550-1, manufactured by Toyobo Co.) by PCR (Saiki, R. K., PCR Protocols, edited by Innis, M. A., et al., 13–20, Academic Press Inc.). Primers used are shown below.

HG46 (SEQ ID NO: 14):
5'-CTTAGATCTATGGACCGCGACTCGTACC-3'
(containing restriction enzyme BglII site)
HG47 (SEQ ID NO: 15):
5'-AGCGAATTCAGTAGCTACTGAGGTACTC-3'
(containing restriction enzyme EcoRI site)

After 0.1 µg of the resulting DNA was reacted with 50 µl of the reaction mixture of 5 U each of restriction enzymes BamHI and EcoRI at 37° C. for 2 hours, extraction with phenol-chloroform was carried out followed by ethanol precipitation. Centrifugation was conducted at 12000 rpm for 10 minutes to recover the precipitates. Likewise 0.1 µg of pTZ19R (OSPTZ-19R, made by Toyobo Co.) was treated to give a linear vector. The vector was ligated with the DNA previously obtained in 10 µl of reaction solution using Ligation Kit (6021, made by Takara Shuzo Co.). The competent cell obtained in paragraph (4) later described was transformed with a part (2 µl) of the reaction mixture to give mycL2-inserted pTZ19-20. A polypeptide (MycL2) having the amino acid sequence shown in FIG. 1 (SEQ ID NO: 2) is synthesized from the open reading frame of mRNA corresponding to the thus obtained DNA. Comparison in amino acid sequence between human L-Myc (Morton, C. C., et al., GENOMICS, 4, 367–375 (1989)) and MycL2 (Robertson, N. G., et al., Nucleic Acids Res., 19, 3129–3137 (1991)) reveals high homology (Score 1289 (71.4%/364aa)).

(2) Preparation of Vector

A heavy metal-inducing HMTII promoter (Karin, M. Haslinger, et al., Cell, 36, 371–329 (1984)) was inserted into pSVneo (Kume, U.-T. et al., J. Mol. Biol., 202, 779–781 (1988)) to give expression vector pSVneoHMT (Nemoto, Y., et al., Gene, 91, 261–265 (1990)) and 0.4 µg of the vector was reacted with 50 µl of 8 U of restriction enzyme BamHI at 37° C. for 2 hours to give a linear vector. The ends of this linear vector were rendered blunt using Blunting Kit (6025, made by Takara Shuzo Co.). The thus obtained vector is named HMT vector.

In order to construct pGal4-MLb and pGal4-MLh, 0.2 µg of pGal4 was reacted at 37° C. for 2 hours with 50 µl of the reaction mixture of 5 U each of restriction enzymes XbaI and BamHI. A linear vector was obtained in a similar manner. This vector is named vector b.

In order to construct pGal4-SM, 0.4 µg of pGal4 was reacted at 37° C. for 2 hours with 50 µl of 8 U of restriction enzyme BamHI. The ends of the thus obtained linear vector was rendered blunt using the Blunting Kit described above. The resulting vector is named vector SM.

Furthermore, 0.2 µg of this vector was reacted at 37° C. for 2 hours with 50 µl of 5 U of restriction enzyme XbaI to give vector s for constructing pGal-MLs.

0.4 µg of pGal4 was reacted at 37° C. for 2 hours with 50 µl of 8 U of restriction enzyme XbaI. The ends of the thus obtained linear vector was rendered blunt using the Blunting Kit described above. Furthermore, 0.2 µg of this vector was reacted at 37° C. for 2 hours with 50 µl of 5 U of restriction enzyme BamHI to give vector hb for constructing pGal-MLhb.

(3) Origin of the Cell Line Used

Human glioma cells U251 (Acta Pathol. Microbiol. Scad., 74, 465–485, 1968; Human Tumor Cells in vitro, in New York, Plenum Publishing Corp., 175–206 (1975)) used was supplied by Dr. M. Rosenblumn (UCSF) (Bodell, W. T., et al., Cancer Res., 45, 3460–3464 (1985); Yoshida, J., et al., Cancer, 50, 410–418 (1982)).

As a culture medium, DMEM (Dulbecco's modified essential medium), 10% FCS (fetal calf serum) and 600 µg/ml glutamine were employed.

(4) Preparation of Competent Cells

E. coli HB101 (ATCC 33694) was inoculated on 5 ml of ψ-broth containing 2% Bacto Tryptone (made by Difco Co.), 0.5% Bacto Yeast extract (made by Difco Co.) and 0.5% $MgSO_4$ followed by shake culture at 37° C. When absorbance at 600 nm reached about 0.3, the entire volume was transferred to 100 ml of ψ-broth. Shake culture was continued at 37° C. until absorbance at 600 nm reached 0.3 to 0.5. After the culture medium was ice cooled for 10 minutes, centrifugation was conducted at 4° C. and 6000 rpm for 5 minutes to collect the cells. The cells were suspended in 10 ml of TfbI solution (30 mM $KOCOCH_3$, 100 mM RbCl, 10 mM $CaCl_2$, 50 mM $MnCl_2$, 15% glycerol, pH 5.8). After allowing to stand at 0° C. for 5 minutes, the suspension was again centrifuged to collect the cells. After the cells were suspended in 2 ml of Tfb2 solution (10 mM MOPS, 75 mM $CaCl_2$, 10 mM RbCl, 15% glycerol, pH 6.5), the suspension was allowed to stand in ice for 15 minutes and 200 µl each was dispensed. After instant freezing on a dry ice-ethanol bath, the suspension was stored at −80° C.

(5) Preparation of MycL2 Expression Vector

In order to excise mycL2 gene from 5 µg of pTZ19-20 obtained in paragraph (1), digestion was effected at 37° C. for 2 hours in 100 µl containing 20 U each of restriction enzymes PstI and EcoRI followed by phenol-chloroform treatment and ethanol precipitation. The recovered precipitates were treated in 50 µl of a solution using Blunting Kit to render the ends of DNA blunt. The major reaction product was subjected to electrophoresis on 0.8% agarose gel to recover a fragment containing mycL2 gene. Using Ligation Kit, 0.1 µg of this fragment was reacted with 0.1 µg of vector HMT in 10 µl of a solution. Using a part (2 µl) thereof, the competent cells obtained in paragraph (4) were transformed to give metallothionein promoter (MT promoter) expression vector pSVneoHMT-ML2.

After 5 µg of pTZ19-20 was digested with restriction enzymes XbaI and BamHI, the digestion product was treated in a manner similar to above to recover a fragment containing mycL2 gene. This fragment was ligated with vector b in a manner similar to above to give β-galactosidase promoter (Gal promoter) expression vector pGal4-MLb.

After 5 µg of pTZ19-20 was digested at 37° C. for 2 hours with 100 µl solution of 20 U of restriction enzyme BamHI, the ends were rendered blunt in a manner similar to above. Furthermore after digestion with XbaI, a fragment containing mycL2 gene was recovered in a similar manner. This fragment was ligated with vector s in a similar manner to give pGal4-MLs.

After 5 µg of pTZ19-20 was digested at 37° C. for 2 hours with 100 µl solution of 20 U of a restriction enzyme HindIII, the ends were rendered blunt in a similar manner. Then 4 µg of this vector was ligated with 1 µg of BamHI linker (4610P, made by Takara Shuzo Co.) in a similar manner followed by phenol-chloroform treatment and ethanol precipitation. After about 4 µg of this vector was digestion with 10 U of XbaI and 20 U of BamHI, a fragment containing mycL2 gene was recovered in a similar manner. This fragment was ligated with vector b in a similar manner to give pGal4-MLh.

After 5 µg of pTZ19-20 was digested at 37° C. for 2 hours with 100 µl solution of 20 U of a restriction enzyme XbaI, the ends were rendered blunt in a manner similar to above. Furthermore after digestion with BamHI, a fragment containing mycL2 gene was recovered in a similar manner. This fragment was ligated with vector hb in a similar manner to give pGal4-MLhb.

In a similar manner 0.1 µg of rat s-myc fragment excised with DraI (Sugiyama, A., et al., Proc. Natl. Acad. Sci. USA, 86, 9144–9148 (1989)) was ligated with 0.1 µg of vector SM in a similar manner to give pGal4-SM.

(6) Transfection of Plasmid into Tumor Cells

Transfection of the plasmid into tumor cells in vitro was effected according to the liposome-mediated transfection (Felgner, P. L., et al., Proc. Natl. Acad. Sci. USA, 84, 7413–7417 (1987)). Lipid (100 µg of liposome) and 1–25 µg of the expression vector (plasmid) obtained by CsCl density gradient centrifugation were suspended in 1.5 ml of 150 mM NaCl, 20 mM HEPES, pH 7.4 (HBS) buffer. The cells which reached a confluent growth on a Petri dish of 100 mφ were washed with 5 ml of HBS and 3 ml of lipid-DNA mixture was supplemented thereto. After the cells were incubated at 37° C. for 5 hours, 10 ml of the culture medium was added thereto. After incubation at 37° C. for 16 hours, 10 ml of fresh culture medium was substituted and the cells were collected 2 to 3 days after. In order to obtain stable transfectants, when using as a selection marker, e.g., neomycin resistance, incubation is performed in a selective medium containing 400 µg/ml neomycin.

(7) Experiment in vitro (i) Preparation of mRNA and Cells for Determination of the Cells Being Dead or Alive After U251 transfectants of 1×10$^6$ per Petri dish were cultured at 37° C. for 6 hours in the presence of 5% $CO_2$ gas, the medium was exchanged with 10 ml of fresh culture medium. After further 4 hours, $ZnSO_4$ was supplemented to become 250 µM (no $ZnSO_4$ was added to the control group). A Petri dish for preparation of MRNA was treated 5 hours after. A Petri dish for determination of dead or alive cells was treated 72 hours after and it was judged by Trypan Blue staining.

(ii) Northern Blotting Analysis

According to the method shown in paragraph (6), transfectant U251ML2 was prepared from human glioma cells U251, using expression vector pSVneoHMT-ML2. The expression level of mycL2 (1.1 kb) was analyzed by Northern blotting so that clones showing various levels of expression were obtained in the presence of 250 µM $ZnSO_4$.

Northern blotting was carried out as follows. About 1 µg of mycL2 ORF fragment was reacted at 15° C. for 2 hours using Nick Translation Kit (manufactured by Takara Shuzo Co.) and 3.7 MBq of α-[$^{32}$P]-dCTP (made by Amersham Co.). The reaction was then terminated. After treating the enzyme at 70° C. for 10 minutes, radioactive-labeled DNA was separated by Sephadex G100 gel filtration. The total RNA was prepared by AGPC method (Chomczynski, P. and Sacchi, N., Anal. Biochem., 162, 156–159 (1987)). That is, 10 ml of solution D (4M guanidine thiocyanate, 25 mM sodium citrate, 0.5% sodium lauroyl sarcocinate, 0.1M mercaptoethanol) was added per 1×10$^7$ cells followed by homogenization with Polytron. Then, 1 ml of 2M sodium acetate, pH 4.0, was added thereto to blend them. Furthermore, 10 ml of saturated aqueous phenol solution was added thereto and 2 ml of chloroform-isoamyl alcohol (49:1) was then added to the mixture. The mixture was transferred to a centrifuging tube, vigorously shaken for 10 seconds, then ice-cooled for 15 minutes and centrifuged at 4° C. and 10,000×g for 20 minutes. The supernatant was recovered and an equal amount of isopropanol was added thereto. After thoroughly mixing, the mixture was allowed to stand at −20° C. for an hour followed by centrifugation at 4° C. and 10,000×g for 20 minutes. To the precipitates was added 3 ml of Solution D. The precipitates were fully dissolved by pipetting. After an equal amount of isopropanol was added to the solution, the mixture was mixed and then allowed to stand at −20° C. for an hour followed by centrifugation at 4° C. and 10,000×g for 10 minutes. The supernatant was discarded and the precipitates were washed with 70% ethanol to give 0.15–0.3 mg of the total RNA. Thereafter poly (A) RNA was prepared as follows. After 1 ml of 10 mM Tris/HCl, pH 7.5, mM EDTA and 0.1% SDS were added to 1 ml of the total RNA, 1 ml of oligotex-dT30 <super> (made by Daiichi Kagaku Yakuhin Co.) was further added to the mixture. The resulting mixture was heated at 65° C. for 5 minutes and then quenched in ice for 3 minutes. After 0.2 ml of 5M NaCl was added to the mixture, incubation at 37° C. for 10 minutes followed. After centrifugation at 15,000 rpm for 3 minutes, the supernatant was carefully removed. The resulting pellets were suspended in 2.5 ml of 10 mM Tris/HCl, pH 7.5, 1 mM EDTA, 0.5M NaCl and 0.1% SDS solution. After centrifugation at 15,000 rpm for 3 minutes, the supernatant was carefully removed. The pellets were suspended in 1 ml of sterile distilled water. The suspension was heated at 65° C. for 5 minutes and then quenched in ice for 3 minutes. The suspension was centrifuged at 15,000 rpm for 3 minutes to give 1.5 to 5 µg of poly (A) RNA=mRNA in the supernatant. The resulting mRNA was subjected to electrophoresis using 1.5% formaldehyde agarose gel. Using Hybond-N (made by Amersham Co.) as a membrane, transfer was effected according to molecular cloning (Cold Spring Harbor laboratory Press, 7, 46–47). Hybridization and autoradiography were carried out according to the molecular cloning (Cold Spring Harbor laboratory Press, 7, 46–52), using the membrane on which RNA had been transferred, and 740 kBq of the previous prepared radioactive-labeled DNA was used for hybridization.

(iii) Determination as to Whether the Cells are Dead or Alive

Using various clones obtained in (ii), the relationship between expression of MycL2 (SEQ ID NO: 2) and dead or alive status of tumor cells was examined. With the clones which did not express MycL2 (SEQ ID NO: 2) even though Zn ions were added thereto, an increase of dead cells was hardly noted in tumor cells, whereas an increase of dead cells was obviously noted with the clones which expressed MycL2 (SEQ ID NO: 2) on a high level.

(iv) Function of MycL2 as a Transcription Factor

Figure 3:
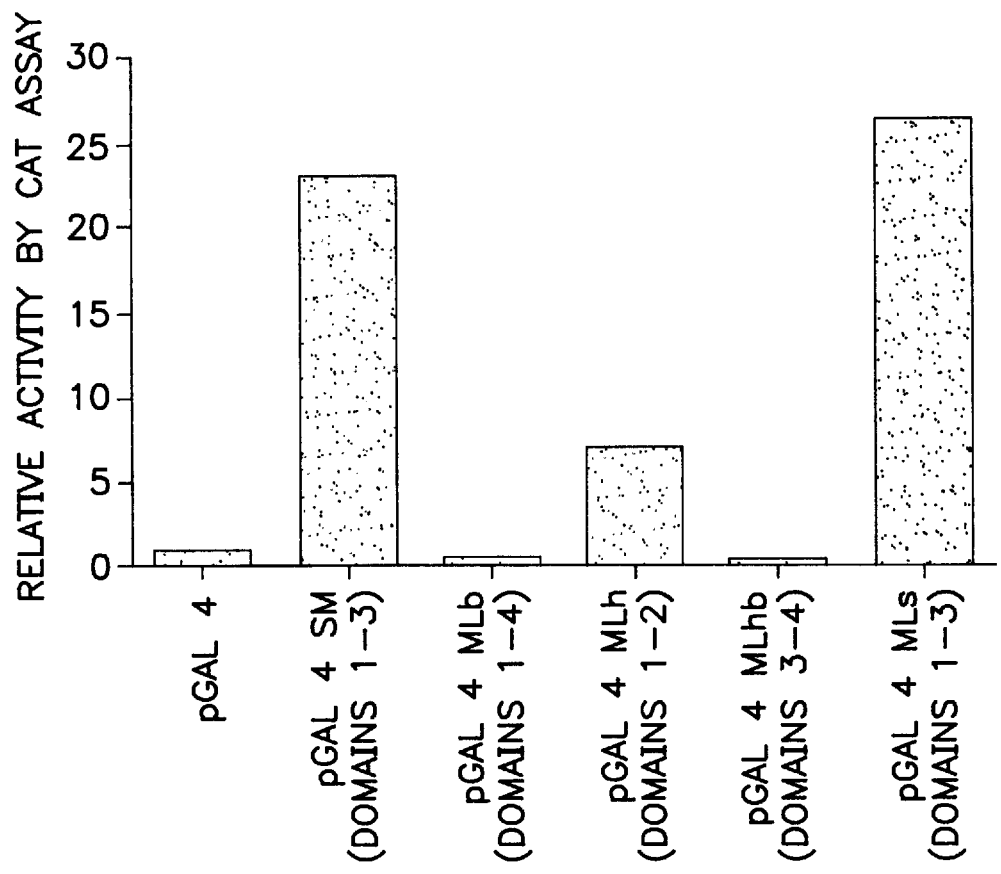
FIG. 3 shows the results of CAT assay performed using an effector plasmid and a reporter plasmid.

In order to survey the mechanism of the function of MycL2 (SEQ ID NO: 2) on a molecular level, the function as a transcription factor which is common in MycL2 (SEQ ID NO: 2) was studied in terms of expression of a chimeric protein. According to the liposome-mediated transfection, 5 µg of the effector plasmid and 5 µg of the reporter plasmid constructed as shown in FIG. 2 were transfected to human glioma cells U251. The cells were collected 48 hours after and the resultant ligate was subjected to chloramphenicol acetyl transferase (CAT) assay. The activity was determined as a ratio to the CAT activity, as a standard, when using pGal4. MycL2 (SEQ ID NO: 2) completely lost its transcription activity when MycL2 (SEQ ID NO: 2) contained its Domain IV (SEQ ID NO: 7) (FIG. 3). Based on the results, disappearance of the transcription activity is attributed to Domain IV (SEQ ID NO: 7) or the region of amino acids 119–191 (SEQ ID NO: 1) containing Domain IV (SEQ ID NO: 7).

Domain IV (SEQ ID NO: 7)

Ser Asp Ser Glu Gly Glu Glu Ile Asp Val

Amino acids 119–191 (SEQ ID NO: 1)

Lys Glu Phe Ala Thr Pro Asp Tyr Thr Pro Glu Leu Glu Ala Gly Asn Leu Ala Pro Ile Phe Pro Cys Leu Leu Gly Glu Pro Lys Ile Gln Ala Cys Ser Arg Ser Glu Ser Pro Ser Asp Ser Glu Gly Glu Glu Ile Asp Val Thr Val Lys Lys Arg Gln Ser Leu Ser Thr Arg Lys Pro Val Ile Ile Ala Val Arg Ala Asp Leu Leu Asp

In order to use DNA having the nucleotide sequence coding for Domain IV (SEQ ID NO: 7) and the sequence of amino acids 119–191 (SEQ ID NO: 1) containing Domain IV (SEQ ID NO: 7) as an agent for preventing the growth of tumor, the recombinant vector bearing this DNA was embedded in liposome and stored.

Furthermore, it was examined as to what activity mycL2, not chimeric protein, has as a whole on transcription. According to this CAT assay, a level of activating the transcription of the transcription factor capable of recognizing the nucleotide sequence of CACGTG can be determined.

Figure 4:
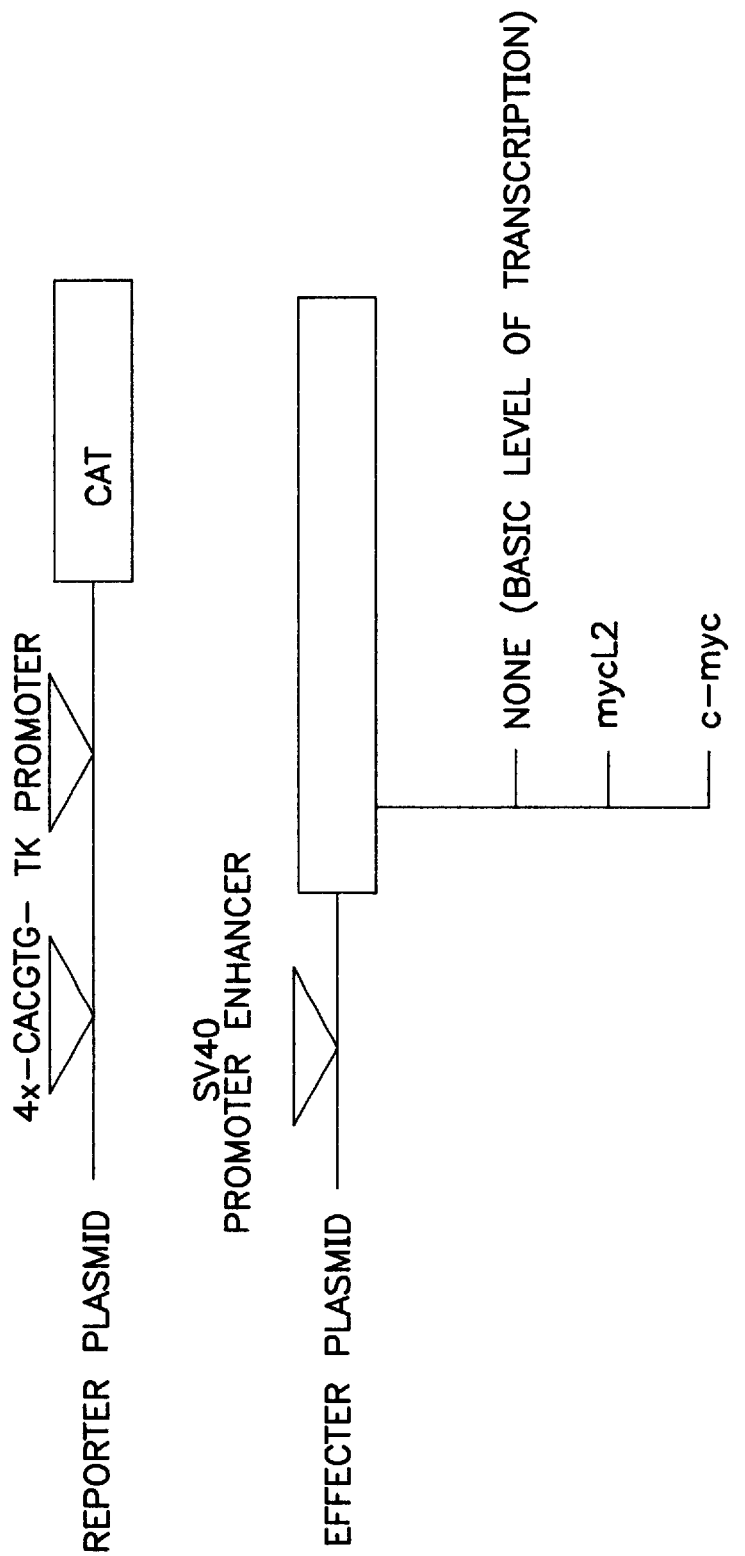
FIG. 4 shows the partial construction of an effector plasmid and a reporter plasmid. In this reporter plasmid, 4x-CACGTG is substituted for 5 Gal 4 binding site of the reporter plasmid shown in FIG. 2.
Figure 5:
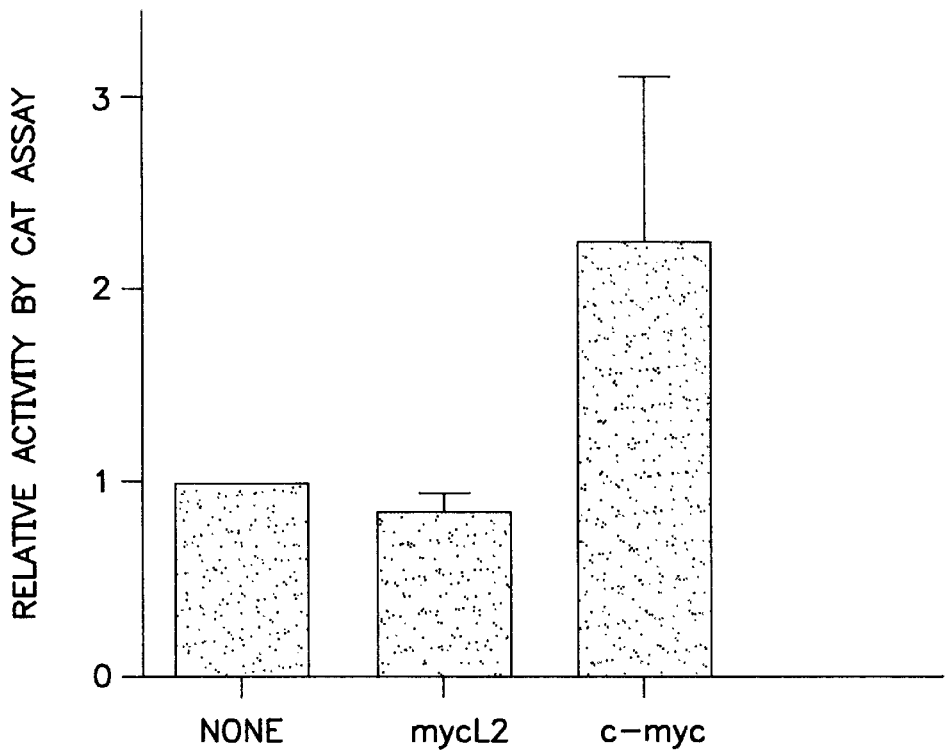
FIG. 5 shows the results of CAT assay performed using the effector plasmid and reporter plasmid shown in FIG. 4.

Using-the liposome-mediated transfection method, 10 μg of the effector plasmid and 5 μg of the reporter plasmid constructed as shown in FIG. 4 were transfected to human glioma cells U251. After incubation for 48 hours, the cells were collected and the resulting lysate was provided for CAT assay. A value obtained by dividing the CAT activity when inserted with each gene of c-myc and mycL2 with the CAT activity when inserted with no gene (basic level of transcription) is made the ability of activating (or inhibiting) the transcription by each gene. Expression of MycL2 is observed toward decreasing the basic level of transcription. It is thus considered that MycL2 would have the function as a transcription inhibitor (FIG. 5).

Figure 6:
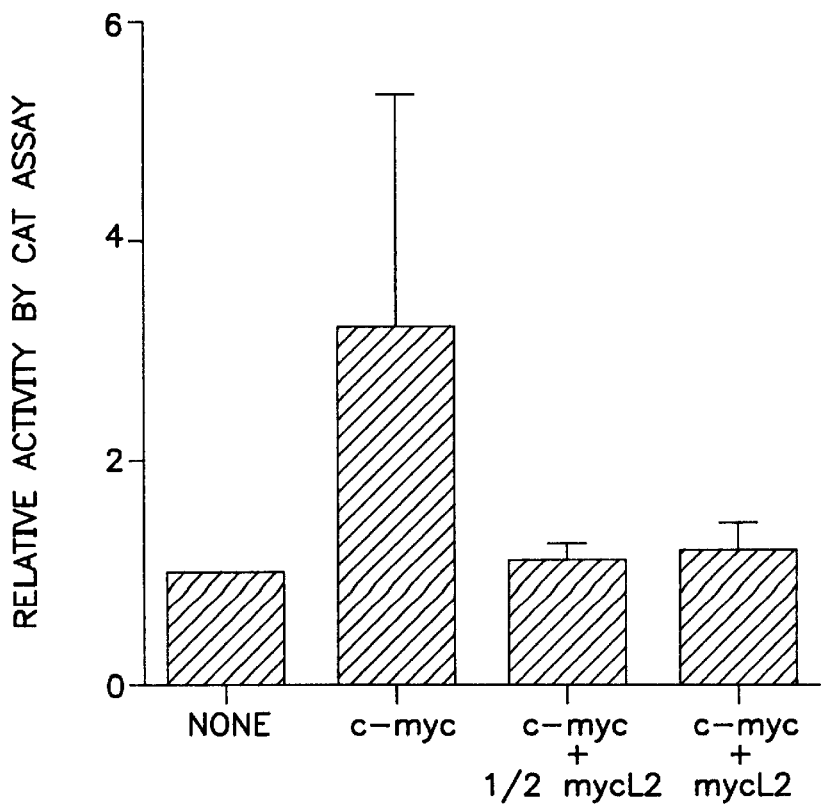
FIG. 6 shows the results c-Myc polypeptide and MycL2 polypeptide transfected to U251 cells to express the polypeptides simultaneously in order to examine the influence of the polypeptides on CAT assay.

Likewise, CAT assay was performed (1) without vector, (2) with 5 μg of c-myc vector, (3) with 5 μg of c-myc vector+2.5 μg of mycL2 vector and (4) with 5 μg of c-myc vector+5 μg of mycL2 vector (FIG. 6). The results reveal that MycL2 inhibits dose-dependently the activation of transcription in the sequence of CACGTG.

What is claimed is:

1. An isolated nucleic acid comprising a nucleotide sequence coding for MycL2 polypeptide, wherein said MycL2 polypeptide comprises the amino acid sequence as shown in SEQ ID NO:2.

2. An isolated nucleic acid sequence coding for MycL2 polypeptide consisting of nucleotide bases 355 through 573 of SEQ ID NO:3.

3. An isolated nucleic acid according to claim 1, which is represented by SEQ ID NO:3.

4. An isolated expression vector comprising the nucleic acid according to claim 1.

5. An isolated expression vector comprising the nucleic acid according to claim 3.

6. A liposome-DNA complex comprising an isolated expression vector according to claim 4 together with liposome.

7. A liposome-DNA complex comprising an isolated expression vector according to claim 5 together with liposome.

8. An isolated DNA sequence consisting of nucleotide residues that encode for the following amino acid sequence:

Ser Asp Ser Glu Gly Gtu Glu Ile Asp Val (SEQ ID NO:7).

9. An isolated DNA sequence consisting of nucleotide residues that encode for the following amino acid sequence:

Lys Glu Phe Ala Thr Pro Asp Tyr Thr Pro Glu Leu Glu Ala Gly Asn Leu Ala Pro Ile Phe Pro Cys Leu Leu Gly Glu Pro Lys Ile Gln Ala Cys Ser Arg Ser Glu Ser Pro Ser Asp Ser Glu Gly Glu Glu Ile Asp Val Thr Val Lys Lys Arg Gln Ser Leu Ser Thr Arg Lys Pro Val Ile Ile Ala Val Arg Ala Asp Leu Leu Asp (SEQ ID NO:1).

10. An isolated expression vector comprising a nucleic acid sequence of claim 2.

11. The DNA sequence of claim 8 wherein said nucleotide residues consist of nucleotide bases 472 through 501 of SEQ ID NO:3.

12. An isolated nucleic acid according to claim 3 wherein T is replaced with U.

13. An isolated expression vector transfected by the DNA sequence of claim 8.

14. An isolated expression vector transfected by the DNA sequence of claim 9.

15. A liposome-DNA complex comprising an isolated expression vector according to claim 13 in liposome.

16. A liposome-DNA complex comprising an isolated expression vector according to claim 14 in liposome.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

```
Lys  Glu  Phe  Ala  Thr  Pro  Asp  Tyr  Thr  Pro  Glu  Leu  Glu  Ala  Gly  Asn
 1              5                        10                       15

Leu  Ala  Pro  Ile  Phe  Pro  Cys  Leu  Leu  Gly  Glu  Pro  Lys  Ile  Gln  Ala
              20                       25                       30

Cys  Ser  Arg  Ser  Glu  Ser  Pro  Ser  Asp  Ser  Glu  Gly  Glu  Glu  Ile  Asp
          35                       40                       45

Val  Thr  Val  Lys  Lys  Arg  Gln  Ser  Leu  Ser  Thr  Arg  Lys  Pro  Val  Ile
     50                       55                       60

Ile  Ala  Val  Arg  Ala  Asp  Leu  Leu  Asp
65                       70
```

( 2 ) INFORMATION FOR SEQ ID NO:2:

( i ) SEQUENCE CHARACTERISTICS:
        ( A ) LENGTH: 358 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
Met  Asp  Arg  Asp  Ser  Tyr  His  His  Tyr  Phe  Tyr  Asp  Tyr  Asp  Gly  Gly
 1              5                        10                       15

Glu  Asp  Phe  Tyr  Arg  Ser  Thr  Thr  Pro  Ser  Glu  Asp  Ile  Trp  Lys  Lys
```

```
                        20                      25                      30

Phe  Glu  Leu  Val  Pro  Pro  Pro  Trp  Asp  Leu  Gly  Pro  Ala  Gly  Asn
              35                      40                      45

Pro  Ala  Leu  Ser  Phe  Gly  Leu  Leu  Glu  Pro  Trp  Pro  Val  Gly  Cys  Ala
         50                      55                      60

Gly  Asp  Glu  Thr  Glu  Ser  Gln  Asp  Tyr  Trp  Lys  Ala  Trp  Asp  Ala  Asn
    65                      70                      75                      80

Tyr  Ala  Ser  Leu  Ile  Arg  Arg  Asp  Cys  Met  Trp  Ser  Gly  Phe  Ser  Thr
                        85                      90                      95

Gln  Glu  Pro  Leu  Glu  Arg  Ala  Val  Ser  Asp  Leu  Leu  Ala  Pro  Gly  Ala
                   100                     105                     110

Pro  Arg  Gly  Tyr  Ser  Pro  Lys  Glu  Phe  Ala  Thr  Pro  Asp  Tyr  Thr  Pro
                   115                     120                     125

Glu  Leu  Glu  Ala  Gly  Asn  Leu  Ala  Pro  Ile  Phe  Pro  Cys  Leu  Leu  Gly
              130                     135                     140

Glu  Pro  Lys  Ile  Gln  Ala  Cys  Ser  Arg  Ser  Glu  Ser  Pro  Ser  Asp  Ser
    145                     150                     155                     160

Glu  Gly  Glu  Glu  Ile  Asp  Val  Thr  Val  Lys  Lys  Arg  Gln  Ser  Leu  Ser
                        165                     170                     175

Thr  Arg  Lys  Pro  Val  Ile  Ile  Ala  Val  Arg  Ala  Asp  Leu  Leu  Asp  Pro
                   180                     185                     190

Arg  Met  Asn  Leu  Phe  His  Ile  Ser  Ile  His  Gln  Gln  His  Asn  Tyr
              195                     200                     205

Ala  Ala  Pro  Phe  Pro  Pro  Glu  Ser  Cys  Phe  Gln  Glu  Gly  Ala  Pro  Lys
         210                     215                     220

Arg  Met  Pro  Pro  Lys  Glu  Ala  Leu  Glu  Arg  Glu  Ala  Pro  Gly  Gly  Lys
    225                     230                     235                     240

Asp  Asp  Lys  Glu  Asp  Glu  Glu  Ile  Val  Ser  Leu  Pro  Pro  Val  Glu  Ser
                        245                     250                     255

Glu  Ala  Ala  Gln  Ser  Cys  Gln  Pro  Lys  Pro  Ile  His  Tyr  Asp  Thr  Glu
                   260                     265                     270

Asn  Trp  Thr  Lys  Lys  Lys  Tyr  His  Ser  Tyr  Leu  Glu  Arg  Lys  Arg  Arg
              275                     280                     285

Asn  Asp  Gln  Arg  Ser  Arg  Phe  Leu  Ala  Leu  Arg  Asp  Glu  Val  Pro  Ala
         290                     295                     300

Leu  Ala  Ser  Cys  Ser  Arg  Val  Ser  Lys  Val  Met  Ile  Leu  Val  Lys  Ala
    305                     310                     315                     320

Thr  Glu  Tyr  Leu  His  Glu  Leu  Ala  Glu  Ala  Glu  Glu  Arg  Met  Ala  Thr
                        325                     330                     335

Glu  Lys  Arg  Gln  Leu  Glu  Cys  Gln  Arg  Arg  Gln  Leu  Gln  Lys  Arg  Ile
                   340                     345                     350

Glu  Tyr  Leu  Ser  Ser  Tyr
                   355
```

( 2 ) INFORMATION FOR SEQ ID NO:3:

( i ) SEQUENCE CHARACTERISTICS:
        ( A ) LENGTH: 1077 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1072

( x i ) SEQUENCE DESCRIPTION: SEQ ID NO:3:

```
ATG GAC CGC GAC TCG TAC CAT CAC TAT TTC TAC GAC TAT GAC GGC GGG        48
Met Asp Arg Asp Ser Tyr His His Tyr Phe Tyr Asp Tyr Asp Gly Gly
 1               5                  10                  15

GAG GAT TTC TAC CGC TCC ACG ACG CCC AGC GAG GAC ATC TGG AAG AAA        96
Glu Asp Phe Tyr Arg Ser Thr Thr Pro Ser Glu Asp Ile Trp Lys Lys
                 20                  25                  30

TTC GAG TTG GTG CCG CCG CCC TGG GAC TTG GGT CCC GCA GCC GGG AAC       144
Phe Glu Leu Val Pro Pro Pro Trp Asp Leu Gly Pro Ala Ala Gly Asn
             35                  40                  45

CCA GCC CTC AGC TTT GGT CTC CTG GAA CCG TGG CCG GTA GGG TGC GCT       192
Pro Ala Leu Ser Phe Gly Leu Leu Glu Pro Trp Pro Val Gly Cys Ala
         50                  55                  60

GGG GAC GAG ACG GAA TCC CAG GAC TAC TGG AAA GCT TGG GAC GCG AAC       240
Gly Asp Glu Thr Glu Ser Gln Asp Tyr Trp Lys Ala Trp Asp Ala Asn
 65                  70                  75                  80

TAC GCC TCC CTC ATC CGC CGT GAC TGC ATG TGG AGC GGC TTC TCC ACC       288
Tyr Ala Ser Leu Ile Arg Arg Asp Cys Met Trp Ser Gly Phe Ser Thr
                 85                  90                  95

CAG GAG CCG CTG GAG AGA GCG GTG AGT GAC CTG CTT GCC GTT GGC GCG       336
Gln Glu Pro Leu Glu Arg Ala Val Ser Asp Leu Leu Ala Val Gly Ala
                100                 105                 110

CCC TCG GGA TAC TCG CCC AAG GAG TTC GCC ACC CCC GAC TAC ACT CCC       384
Pro Ser Gly Tyr Ser Pro Lys Glu Phe Ala Thr Pro Asp Tyr Thr Pro
            115                 120                 125

GAG CTC GAA GCC GGC AAC CTA GCG CCC ATC TTC CCC TGT TTG TTG GGC       432
Glu Leu Glu Ala Gly Asn Leu Ala Pro Ile Phe Pro Cys Leu Leu Gly
        130                 135                 140

GAG CCC AAG ATC CAG GCC TGC TCC AGG TCT GAG AGC CCA AGC GAC TCC       480
Glu Pro Lys Ile Gln Ala Cys Ser Arg Ser Glu Ser Pro Ser Asp Ser
145                 150                 155                 160

GAG GGT GAA GAA ATC GAC GTG ACA GTA AAG AAG AGG CAG TCT TTG AGT       528
Glu Gly Glu Glu Ile Asp Val Thr Val Lys Lys Arg Gln Ser Leu Ser
                165                 170                 175

ACG CGG AAG CCA GTC ATC ATC GCG GTG CGT GCA GAC CTT CTG GAT CCC       576
Thr Arg Lys Pro Val Ile Ile Ala Val Arg Ala Asp Leu Leu Asp Pro
            180                 185                 190

CGC ATG AAT CTC TTC CAC ATC TCC ATC CAC CAG CAA CAG CAC AAC TAT       624
Arg Met Asn Leu Phe His Ile Ser Ile His Gln Gln Gln His Asn Tyr
        195                 200                 205

GCT GCC CCT TTT CCT CCA GAA AGC TGC TTC CAA GAA GGG CCT CCA AAG       672
Ala Ala Pro Phe Pro Pro Glu Ser Cys Phe Gln Glu Gly Pro Pro Lys
        210                 215                 220

AGG ATC CCC CCA AAA GAG GCT CTA GAG AGA GAA GCT CCA GGG GGA AAG       720
Arg Ile Pro Pro Lys Glu Ala Leu Glu Arg Glu Ala Pro Gly Gly Lys
225                 230                 235                 240

GAT GAT AAG GAA GAT GAA GAG ATT GTG AGC CTC CCA CCT GTA GAA AGT       768
Asp Asp Lys Glu Asp Glu Glu Ile Val Ser Leu Pro Pro Val Glu Ser
                245                 250                 255

GAG GCT GCC CAG TCC TGC CAG CCC AAA CCC ATC CAT TAT GAT ACT GAG       816
Glu Ala Ala Gln Ser Cys Gln Pro Lys Pro Ile His Tyr Asp Thr Glu
            260                 265                 270

AAT TGG ACC AAG AAG AAG TAC CAC AGC TAC CTG GAG CGC AAG AGA CGG       864
Asn Trp Thr Lys Lys Lys Tyr His Ser Tyr Leu Glu Arg Lys Arg Arg
        275                 280                 285

AAT GAT CAA CGT TCG CGG TTC TTG GCC CTG AGG GAC GAG GTA CCC GCC       912
Asn Asp Gln Arg Ser Arg Phe Leu Ala Leu Arg Asp Glu Val Pro Ala
        290                 295                 300

CTG GCC AGC TGC TCT AGG GTT TCC AAA GTA ATG ATC CTA GTC AAG GCC       960
Leu Ala Ser Cys Ser Arg Val Ser Lys Val Met Ile Leu Val Lys Ala
```

```
305                         310                         315                         320
ACG  GAA  TAC  TTA  CAT  GAA  CTG  GCG  GAA  GCC  GAG  GAG  AGG  ATG  GCT  ACG    1008
Thr  Glu  Tyr  Leu  His  Glu  Leu  Ala  Glu  Ala  Glu  Glu  Arg  Met  Ala  Thr
                    325                      330                      335

GAG  AAA  AGG  CAG  CTC  GAA  TGC  CAG  CGA  CGG  CAA  TTG  CAG  AAA  AGA  ATT    1056
Glu  Lys  Arg  Gln  Leu  Glu  Cys  Gln  Arg  Arg  Gln  Leu  Gln  Lys  Arg  Ile
               340                      345                      350

GAG  TAC  CTC  AGT  AGC  TAC  TGA                                                  1077
Glu  Tyr  Leu  Ser  Ser  Tyr
          355
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:4:

```
Met  Asp  Arg  Asp  Ser  Tyr  His  His  Tyr  Phe  Tyr  Asp  Tyr  Asp  Gly  Gly
1                   5                        10                       15

Glu  Asp  Phe  Tyr
               20
```

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

```
Ser  Thr  Thr  Pro  Ser  Glu  Asp  Ile  Trp  Lys  Lys  Phe  Glu  Leu  Val  Pro
1                   5                        10                       15

Pro
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:6:

```
Asp  Cys  Met  Trp  Ser  Gly  Phe  Ser  Thr  Gln
1                   5                        10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide (v) FRAGMENT TYPE: internal (xi) SEQUENCE DESCRIPTION: SEQ ID NO:7:

Ser Asp Ser Glu Gly Glu Glu Ile Asp Val
1               5                   10

(2) INFORMATION FOR SEQ ID NO:8:

(i) SEQUENCE CHARACTERISTICS:
 (A) LENGTH: 10 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:8:

Ile His Gln Gln Gln His Asn Tyr Ala Ala
1               5                   10

(2) INFORMATION FOR SEQ ID NO:9:

(i) SEQUENCE CHARACTERISTICS:
 (A) LENGTH: 23 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:9:

Tyr Asp Thr Glu Asn Trp Thr Lys Lys Lys Tyr His Ser Tyr Leu Glu
1               5                   10                  15

Arg Lys Arg Arg Asn Asp Gln
            20

(2) INFORMATION FOR SEQ ID NO:10:

(i) SEQUENCE CHARACTERISTICS:
 (A) LENGTH: 32 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:10:

Arg Ser Arg Phe Leu Ala Leu Arg Asp Glu Val Pro Ala Leu Ala Ser
1               5                   10                  15

Cys Ser Arg Val Ser Lys Val Met Ile Leu Val Lys Ala Thr Glu Tyr
            20                  25                  30

(2) INFORMATION FOR SEQ ID NO:11:

(i) SEQUENCE CHARACTERISTICS:
 (A) LENGTH: 22 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:11:

Met Ala Thr Glu Lys Arg Gln Leu Glu Cys Gln Arg Arg Gln Leu Gln
1               5                   10                  15

```
       Lys  Arg  Ile  Glu  Tyr  Leu
                      20
```

( 2 ) INFORMATION FOR SEQ ID NO:12:

( i ) SEQUENCE CHARACTERISTICS:
         ( A ) LENGTH: 4 amino acids
         ( B ) TYPE: amino acid
         ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
       Ser  Pro  Thr  Ser
       1
```

( 2 ) INFORMATION FOR SEQ ID NO:13:

( i ) SEQUENCE CHARACTERISTICS:
         ( A ) LENGTH: 5 amino acids
         ( B ) TYPE: amino acid
         ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
       Thr  Pro  Pro  Leu  Ser
       1                   5
```

( 2 ) INFORMATION FOR SEQ ID NO:14:

( i ) SEQUENCE CHARACTERISTICS:
         ( A ) LENGTH: 28 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:14:

CTTAGATCTA TGGACCGCGA CTCGTACC                    28

( 2 ) INFORMATION FOR SEQ ID NO:15:

( i ) SEQUENCE CHARACTERISTICS:
         ( A ) LENGTH: 28 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:15:

AGCGAATTCA GTAGCTACTG AGGTACTC                    28